(12) United States Patent
Chin et al.

(10) Patent No.: US 8,231,374 B2
(45) Date of Patent: *Jul. 31, 2012

(54) EXTRUSION APPARATUS FOR MAKING MULTILAYER ARTICLES

(75) Inventors: Albert K Chin, Palo Alto, CA (US);
John Jianhua Chen, Plymouth, MN (US); Thomas A. Svatek, Carlisle, MA (US); Ronald A Sahatjian, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 100 days.

This patent is subject to a terminal disclaimer.

(21) Appl. No.: 12/770,333

(22) Filed: Apr. 29, 2010

(65) Prior Publication Data

US 2010/0203181 A1 Aug. 12, 2010

Related U.S. Application Data

(60) Continuation of application No. 12/032,054, filed on Feb. 15, 2008, now Pat. No. 7,713,047, which is a division of application No. 11/184,494, filed on Jul. 19, 2005, now abandoned, which is a division of application No. 10/351,695, filed on Jan. 27, 2003, now Pat. No. 6,951,675.

(51) Int. Cl.
*B29C 47/06* (2006.01)
*B29C 47/20* (2006.01)

(52) U.S. Cl. .......... 425/133.1; 425/192 R; 425/380; 425/462; 425/467

(58) Field of Classification Search .......... 425/133.1, 425/192 R, 380, 462, 467
See application file for complete search history.

(56) References Cited

U.S. PATENT DOCUMENTS

| | | | |
|---|---|---|---|
| 3,308,508 A | 3/1967 | Schrenk |
| 3,334,382 A | 8/1967 | Lefevre |
| 3,365,750 A | 1/1968 | Donald |
| 3,561,493 A | 2/1971 | Maillard et al. |
| 3,618,614 A | 11/1971 | Flynn |
| 3,924,634 A | 12/1975 | Taylor et al. |
| 3,993,812 A | 11/1976 | Debbas et al. |
| 4,044,180 A | 8/1977 | Baker |
| 4,047,850 A | 9/1977 | Berthelot |
| 4,174,783 A | 11/1979 | Abe et al. |

(Continued)

FOREIGN PATENT DOCUMENTS

DE 2848854 5/1979

(Continued)

OTHER PUBLICATIONS

Anon. "Rigid plastics are getting a foot in the kitchen door." Chemical Week, pp. 10-11, Oct. 12, 1983.

*Primary Examiner* — Yogendra Gupta
*Assistant Examiner* — Joseph Leyson
(74) *Attorney, Agent, or Firm* — Seager, Tufte & Wickhem, LLC

(57) ABSTRACT

In certain aspects of the invention, an extrusion apparatus for making a multilayer article includes multiple discs, each of which has at least one passageway configured to permit fluid flow therethrough in a flow direction. At least one of the discs includes a cone shaped portion extending substantially parallel to the flow direction.

19 Claims, 11 Drawing Sheets

U.S. PATENT DOCUMENTS

| | | | |
|---|---|---|---|
| 4,182,457 A | 1/1980 | Yamada et al. |
| 4,211,741 A | 7/1980 | Ostoich |
| 4,244,914 A | 1/1981 | Ranalli et al. |
| 4,282,876 A | 8/1981 | Flynn |
| 4,296,156 A | 10/1981 | Lustig et al. |
| 4,327,736 A | 5/1982 | Inoue |
| 4,335,723 A | 6/1982 | Patel |
| 4,409,364 A | 10/1983 | Schmukler et al. |
| 4,424,242 A | 1/1984 | Barbee |
| 4,451,292 A | 5/1984 | Hall et al. |
| 4,472,129 A | 9/1984 | Siard |
| 4,484,971 A | 11/1984 | Wang |
| 4,490,421 A | 12/1984 | Levy |
| 4,578,024 A | 3/1986 | Sicka et al. |
| 4,596,563 A | 6/1986 | Pande |
| 4,627,844 A | 12/1986 | Schmitt |
| 4,634,615 A | 1/1987 | Versteegh et al. |
| 4,636,346 A | 1/1987 | Gold et al. |
| 4,636,442 A | 1/1987 | Beavers et al. |
| 4,640,852 A | 2/1987 | Ossian |
| 4,648,871 A | 3/1987 | Jacob |
| 4,656,070 A | 4/1987 | Nyberg et al. |
| 4,677,017 A | 6/1987 | DeAntonis et al. |
| 4,686,124 A | 8/1987 | Onohara et al. |
| 4,753,765 A | 6/1988 | Pande |
| 4,778,697 A | 10/1988 | Genske et al. |
| 4,790,831 A | 12/1988 | Skribiski |
| 4,814,231 A | 3/1989 | Onohara et al. |
| 4,816,339 A | 3/1989 | Tu et al. |
| 4,818,592 A | 4/1989 | Ossian |
| 4,824,618 A | 4/1989 | Strum et al. |
| 4,834,721 A | 5/1989 | Onohara et al. |
| 4,840,623 A | 6/1989 | Quackenbush |
| RE32,983 E | 7/1989 | Levy |
| 4,863,426 A | 9/1989 | Ferragamo et al. |
| 4,880,682 A | 11/1989 | Hazelton et al. |
| 4,906,244 A | 3/1990 | Pinchuk et al. |
| 4,917,088 A | 4/1990 | Crittenden |
| 4,932,956 A | 6/1990 | Reddy et al. |
| 4,952,357 A | 8/1990 | Euteneuer |
| 4,963,306 A | 10/1990 | Weldon |
| 4,994,047 A | 2/1991 | Walker et al. |
| 5,041,086 A | 8/1991 | Koenig et al. |
| 5,059,269 A | 10/1991 | Hu et al. |
| 5,071,686 A | 12/1991 | Genske et al. |
| 5,076,776 A | 12/1991 | Yamada et al. |
| 5,093,164 A | 3/1992 | Bauer et al. |
| 5,094,799 A | 3/1992 | Takashige et al. |
| 5,100,721 A | 3/1992 | Akao |
| 5,108,415 A | 4/1992 | Pinchuk et al. |
| 5,125,913 A | 6/1992 | Quackenbush |
| 5,156,857 A | 10/1992 | Wang et al. |
| 5,171,221 A | 12/1992 | Samson |
| 5,195,969 A | 3/1993 | Wang et al. |
| 5,201,706 A | 4/1993 | Noguchi et al. |
| 5,223,205 A | 6/1993 | Jackowski et al. |
| 5,254,090 A | 10/1993 | Lombardi et al. |
| 5,270,086 A | 12/1993 | Hamlin |
| 5,277,199 A | 1/1994 | DuBois et al. |
| 5,290,306 A | 3/1994 | Trotta |
| 5,304,197 A | 4/1994 | Pinchuk et al. |
| 5,306,246 A | 4/1994 | Sahatjian et al. |
| 5,318,041 A | 6/1994 | DuBois et al. |
| 5,330,428 A | 7/1994 | Wang et al. |
| 5,330,429 A | 7/1994 | Noguchi et al. |
| 5,344,401 A | 9/1994 | Radisch et al. |
| 5,356,709 A | 10/1994 | Woo et al. |
| 5,358,486 A | 10/1994 | Saab |
| 5,366,442 A | 11/1994 | Wang et al. |
| 5,417,671 A | 5/1995 | Jackson |
| 5,427,842 A | 6/1995 | Bland et al. |
| 5,439,454 A | 8/1995 | Lo et al. |
| 5,478,320 A | 12/1995 | Trotta |
| 5,509,899 A | 4/1996 | Fan et al. |
| 5,512,051 A | 4/1996 | Wang et al. |
| 5,556,383 A | 9/1996 | Wang et al. |
| 5,562,127 A | 10/1996 | Fanselow et al. |
| 5,587,125 A | 12/1996 | Roychowdhury |
| 5,613,979 A | 3/1997 | Trotta et al. |
| 5,620,649 A | 4/1997 | Trotta |
| 5,669,920 A | 9/1997 | Conley et al. |
| 5,690,672 A | 11/1997 | Cohen |
| 5,755,690 A | 5/1998 | Saab |
| 5,769,817 A | 6/1998 | Burgmeier |
| 5,792,105 A | 8/1998 | Lin et al. |
| 5,797,877 A | 8/1998 | Hamilton et al. |
| 5,820,594 A | 10/1998 | Fontirroche et al. |
| 5,824,173 A | 10/1998 | Fontirroche et al. |
| 5,833,657 A | 11/1998 | Reinhardt et al. |
| 5,843,032 A | 12/1998 | Kastenhofer |
| 5,851,464 A | 12/1998 | Davila et al. |
| 5,871,468 A | 2/1999 | Kramer et al. |
| 5,879,369 A | 3/1999 | Ishida |
| 5,908,406 A | 6/1999 | Ostapchenko et al. |
| 5,961,765 A | 10/1999 | Kastenhofer |
| 6,004,289 A | 12/1999 | Saab |
| 6,010,521 A | 1/2000 | Lee et al. |
| 6,027,477 A | 2/2000 | Kastenhofer |
| 6,059,751 A | 5/2000 | Ostapchenko et al. |
| 6,086,556 A | 7/2000 | Hamilton et al. |
| 6,124,007 A | 9/2000 | Wang et al. |
| 6,132,824 A | 10/2000 | Hamlin |
| 6,136,258 A | 10/2000 | Wang et al. |
| 6,136,394 A | 10/2000 | Karsten |
| 6,165,166 A | 12/2000 | Samuelson et al. |
| 6,242,063 B1 | 6/2001 | Ferrera et al. |
| 6,319,228 B1 | 11/2001 | Kastenhofer |
| 6,335,101 B1 | 1/2002 | Haeger et al. |
| 6,343,919 B1 | 2/2002 | Rodriguez et al. |
| 6,444,324 B1 | 9/2002 | Yang et al. |
| 6,447,835 B1 | 9/2002 | Wang et al. |
| 6,464,683 B1 | 10/2002 | Samuelson et al. |
| 6,471,673 B1 | 10/2002 | Kastenhofer |
| 6,482,348 B1 | 11/2002 | Wang et al. |
| 6,488,655 B1 | 12/2002 | Wantink et al. |
| 6,638,461 B2 | 10/2003 | Davidson et al. |
| 6,951,675 B2 | 10/2005 | Chin et al. |
| 7,713,047 B2 * | 5/2010 | Chin et al. ............. 425/133.1 |
| 2001/0043998 A1 | 11/2001 | Chen et al. |
| 2002/0165523 A1 | 11/2002 | Chin et al. |
| 2003/0020206 A1 * | 1/2003 | Davidson et al. ........ 264/173.11 |
| 2004/0078052 A1 | 4/2004 | St. Pierre et al. |
| 2005/0266109 A1 | 12/2005 | Chin et al. |

FOREIGN PATENT DOCUMENTS

| | | |
|---|---|---|
| DE | 3638828 | 5/1988 |
| EP | 0101213 | 2/1984 |
| EP | 0101216 | 2/1984 |
| EP | 0201331 | 11/1986 |
| EP | 0174206 | 12/1986 |
| EP | 0276908 | 8/1988 |
| EP | 0292587 | 11/1988 |
| EP | 0095521 A1 | 12/1989 |
| EP | 0420488 | 4/1991 |
| EP | 0428479 | 5/1991 |
| EP | 0457456 | 11/1991 |
| EP | 0461474 | 12/1991 |
| EP | 0955211 | 11/1999 |
| EP | 0803264 B1 | 12/2002 |
| FR | 998035 | 1/1952 |
| FR | 2328482 | 5/1977 |
| GB | 1533204 | 11/1978 |
| GB | 1556242 | 11/1979 |
| GB | 2078114 | 1/1981 |
| GB | 1600963 | 10/1981 |
| GB | 2077111 | 12/1981 |
| GB | 2140437 | 11/1984 |
| GB | 2163386 | 2/1986 |
| JP | 51084877 | 7/1976 |
| JP | 5345353 | 12/1978 |
| JP | 58038778 | 3/1983 |
| JP | 2043036 | 2/1990 |
| JP | 3277374 | 12/1991 |
| JP | 434590 | 2/1992 |

| | | | | | | |
|---|---|---|---|---|---|---|
| JP | 4259537 | 9/1992 | | WO | 9604951 | 2/1996 |
| SU | 1477423 | 5/1989 | | WO | 9732624 | 9/1997 |
| WO | 8401327 | 4/1984 | | WO | 9912586 | 3/1999 |
| WO | 9104068 | 4/1991 | | WO | 0132398 | 5/2001 |
| WO | 9211893 | 7/1992 | | WO | 02056930 | 7/2002 |
| WO | 9219316 | 11/1992 | | | | |

* cited by examiner

EXTRUSION APPARATUS FOR MAKING MULTILAYER ARTICLES

CROSS-REFERENCE TO RELATED APPLICATION

This application is a continuation of U.S. patent Ser. No. 12/032,054, filed Feb. 15, 2008, now U.S. Pat. No. 7,713,047 which is a divisional application of and claims priority under 35 U.S.C. §120 to U.S. patent application Ser. No. 11/184,494, filed Jul. 19, 2005, now abandoned, which is a divisional application of and claims priority under 35 U.S.C. §120 to U.S. patent application Ser. No. 10/351,695, filed Jan. 27, 2003, now U.S. Pat. No. 6,951,675. Each of the above-noted patent applications is hereby incorporated by reference.

TECHNICAL FIELD

This invention relates to extrusion apparatus for making multilayer articles.

BACKGROUND

Medical procedures can utilize a balloon in different ways. As an example, in some procedures a balloon is used to open an occluded lumen, as in angioplasty. As another example, in certain procedures a balloon is used to position another medical implement, such as a stent or graft, within a lumen. As additional example, a balloon is used to selectively block a passageway. In additional examples, a balloon is used in various combinations of these procedures.

In some cases, the balloon is positioned on the end of a catheter shaft. The balloon is typically wrapped around the catheter shaft to reduce the radial profile for easier insertion. The catheter is then threaded through the body to position the balloon at a location of treatment and the balloon is inflated. Finally, the balloon is deflated and the catheter is withdrawn from the body.

SUMMARY

The invention relates to multilayer medical devices, such as multilayer balloons.

In one aspect, the invention features an article that is capable of being stretch-molded into a balloon. The balloon has a wall with at least three coextruded layers. One coextruded layer includes a first polymer, and another coextruded layer includes a different polymer. The difference between the apparent shear viscosities of the polymers is at least about 50 Pascal-seconds.

In another aspect, the invention features a balloon that has a burst strength of at least about 10,000 psi. The balloon has a wall with at least three coextruded layers. One coextruded layer includes a first polymer, and another coextruded layer includes a different polymer. The difference between the apparent shear viscosities of the polymers is at least about 50 Pascal-seconds.

In a further aspect, the invention features a balloon that is capable of passing the multiple inflation test. The balloon has a wall with at least three coextruded layers. One coextruded layer includes a first polymer, and another coextruded layer includes a different polymer. The difference between the apparent shear viscosities of the polymers is at least about 50 Pascal-seconds.

In one aspect, the invention features an extrusion apparatus for making a multilayer article. The apparatus includes two sections and a plurality of discs between the sections. Each of the discs has at least one passageway configured to permit fluid flow therethrough in a flow direction. The thickness of at least one of the discs in the flow direction is about one inch or less, and the passageway of at least one of the discs is spiral shaped.

In another aspect, the invention features an extrusion apparatus for making a multilayer article. The apparatus includes two sections and a plurality of discs between the first and second sections. Each of the discs has at least one passageway configured to permit fluid flow therethrough in a flow direction. The thickness of at least one of the discs in the flow direction is about one inch or less, and at least one of the discs includes a cone shaped portion extending substantially parallel to the flow direction.

In a further aspect, the invention features a method that includes coextruding at least three polymer layers to form an article. One coextruded layer includes a first polymer, and another coextruded layer includes a different polymer. The difference between the apparent shear viscosities of the polymers is at least about 50 Pascal-seconds.

In one aspect, the invention features a method that includes coextruding multiple polymer layers through corresponding multiple discs to form an article having a wall comprising multiple coextruded polymer layers. At least one of the discs has a spiral shaped passageway.

In another aspect, the invention features a method that includes coextruding multiple polymer layers through corresponding multiple discs to form an article having a wall comprising multiple coextruded polymer layers. At least one of the discs has a passageway configured to permit flow therethrough in a flow direction, and at least one of the discs includes a cone shaped portion extending substantially parallel to the flow direction.

Embodiments may also include one or more of the following features.

The difference between the shear viscosities of the polymers can be at least about 75 Pascal-seconds (e.g., at least about 100 Pascal-seconds).

At least two (e.g., at least three) of the coextruded layers can be adjacent layers.

The article can be in the shape of a tube, a catheter shaft or a balloon.

One polymer can be, for example, a polyester. Another polymer can be, for example, a different polyester. Examples of polyesters include PETs and PBTs.

One polymer can be, for example, a polyamide. Another polymer can be, for example, a different polyamide. Examples of polyamides include nylon 11, nylon 6, nylon 6/10, nylon 6/12, nylon 12 and aromatic nylons.

After being formed into a balloon, the article can have a burst strength of at least about 10,000 psi.

After being formed into a balloon, the article can pass the multiple inflation test. The article can be capable of being stretch-molded to form a balloon. Examples of balloons include coronary balloons, aortic balloons, peripheral balloons, reperfusion balloons, endoscopy balloons, urology balloons and neurology balloons.

The article can include at least four (e.g., at least five, at least six, at least seven, at least eight, at least nine, at least ten, at least 11, at least 12, at least 13, etc.) coextruded layers.

In certain embodiments, the wall structure can have a relatively high degree of uniformity. In some embodiments, this can, for example, reduce balloon failure due to uneven stress and/or strain placed on the balloon during formation (e.g., stretch-molding) and/or use (e.g., during inflation). The extrusion apparatuses, methods and materials (e.g., at least two adjacent coextruded layers formed of materials having a relatively large difference in apparent shear viscosity) can be used for such wall structures.

In some embodiments, the wall structure can be formed of relatively well defined layers with relatively little intermixing between adjacent layers and/or relatively little (e.g., no) contact between alternate layers. In certain embodiments, this can, for example, reduce balloon failure due to uneven stress and/or strain placed on the balloon during formation (e.g., stretch molding) and/or use (e.g., during inflation). The extrusion apparatuses, methods and materials (e.g., at least two adjacent coextruded layers formed of materials having a relatively large difference in apparent shear viscosity) can be used for such wall structures.

In certain embodiments, a wall structure having one or more layers formed of relatively high molecular weight polymer material(s) can provide a medical device, such as a multilayer balloon, with desirable properties. For example, the medical device can exhibit good hoop strength, toughness, crack resistance and resistance to pinhole formation. The wall structure can be at least partially or entirely formed of coextruded layers of polymer material(s). The extrusion apparatuses, methods and materials (e.g., at least two adjacent coextruded layers formed of materials having a relatively large difference in apparent shear viscosity) can be used for such wall structures.

In some embodiments, the medical device (e.g., balloon) can undergo no substantial physical degradation when subjected to conditions that are as stressful or more stressful than the intended use conditions of the medical device. The extrusion apparatuses, methods and materials (e.g., at least two adjacent coextruded layers formed of materials having a relatively large difference in apparent shear viscosity) can be used to prepare such medical devices.

Features, objects and advantages of the invention are in the description, drawings and claims.

DETAILED DESCRIPTION

Figure 1:
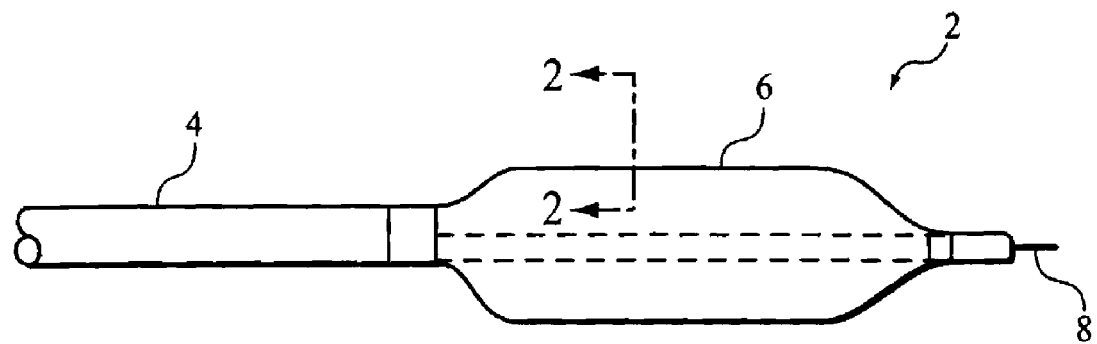
FIG. 1 is a side view of an embodiment of a balloon catheter system.

FIG. 1 shows an embodiment of a balloon catheter system 2 including a catheter shaft 4 carrying an inflatable balloon 6. A guide wire 8 can be used to deliver balloon 6 to a treatment area (e.g., a coronary artery). Examples of catheter systems are described in, for example, U.S. Pat. Nos. 5,195,969 and 5,270,086, which are hereby incorporated by reference. An example of a balloon catheter system is the Ranger® system, commercially available from Boston Scientific Scimed, Maple Grove, Minn.

Figure 2:
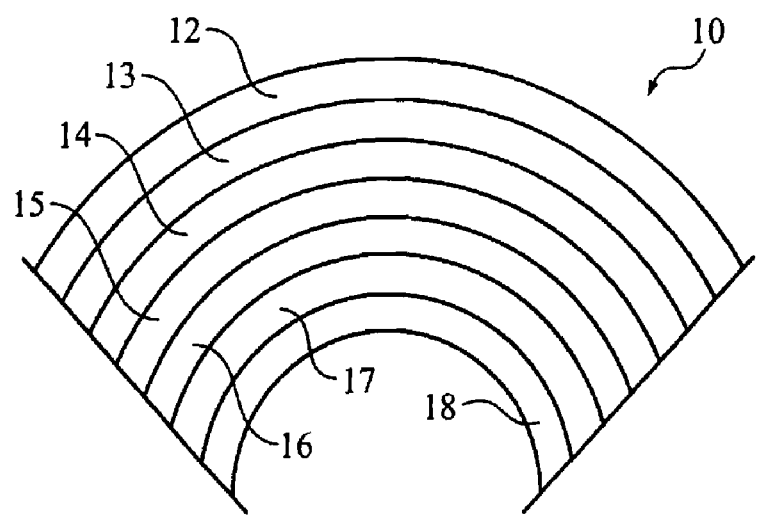
FIG. 2 is a cross-section through a section of an embodiment of a wall of a balloon taken along the line 2-2 in FIG. 1.

FIG. 2 is a cross-sectional view of a wall 10 of balloon 6 having coextruded polymer layers 12, 13, 14, 15, 16, 17 and 18. For at least one pair of adjacent coextruded layers (e.g., layer 13/layer 14, layer 14/layer 15, layer 15/layer 16, layer 16/layer 17, and/or layer 17/layer 18), the difference in the apparent shear viscosity of the polymer that forms one of the layers and the apparent shear viscosity of the polymer that forms the other layer in the pair is relatively large. In some embodiments, for at least one pair of adjacent coextruded layers in wall 10, the difference between the apparent shear viscosity of the polymer that forms one of the layers in the pair and the apparent shear viscosity of the polymer that forms the other layer in the pair is at least about 50 Pascal-seconds (e.g., at least about 75 Pascal-seconds, at least about 100 Pascal-seconds, at least about 125 Pascal-seconds, at least about 150 Pascal-seconds).

The apparent shear viscosity of a polymer is determined as follows. The polymer is placed in a capillary rheometer (Kayeness Galaxy V, Model 8052) at about room temperature. The temperature of the capillary rheometer is set to 30° C. above the melt temperature of the polymer, and the capillary rheometer is heated to that temperature, as reported by the capillary rheometer. The rheometer is held at that temperature for 10 minutes. The polymer is then extruded using a pressure such that the shear rate of the polymer, as reported by the capillary rheometer, is 660 per second. The shear viscosity of the polymer that is reported by the capillary rheometer is referred to herein as the apparent shear viscosity of the polymer.

The melt temperature of a polymer is determined as follows. The polymer is placed in a differential scanning calorimeter (Model DSC7, Perkin-Elmer, Shelton, Conn.). The polymer is then heated to at least a temperature sufficient to cause all the polymer to melt. The temperature that the calorimeter reports as the melt temperature of the polymer is referred to herein as the melt temperature. In some embodiments, the calorimeter may report more than one melt temperature for a given polymer. In these embodiments, the highest of the melt temperatures reported by the calorimeter is referred to herein as the melt temperature of the polymer. Moreover, in embodiments in which a blend of polymers is used (see discussion below), the calorimeter may report more than one melt temperature. In these embodiments, the highest of the melt temperatures reported by the calorimeter is referred to herein as the melt temperature of the polymer.

In general, for each layer in wall 10, the polymer that forms the layer can be selected as desired. Such polymers include, for example, homopolymers and copolymers. As an example, in some embodiments, one or both layers in a pair of adjacent coextruded layers can be formed of a homopolymer. As another example, in certain embodiments, one or both layers in a pair of adjacent coextruded layers can be formed of a copolymer.

In some embodiments, one of the layers in a pair of adjacent coextruded layers is formed of a certain type (e.g., grade) of a polymer, and the other layer in the pair is formed of a different type (e.g., grade) of the same polymer. As an example, in certain embodiments, one of the layers in a pair of adjacent coextruded layers can be formed of one type of polyester, and the other layer in the pair can be formed of a different type of polyester. As another example, in some embodiments, one of the layers in a pair of adjacent coextruded layers can be formed of one type of polyamide, and the other layer in the pair can be formed of a different type of polyamide.

In certain embodiments, the layers in a pair of adjacent coextruded layers are formed of different polymers. As an example, in some embodiments, one of the layers in a pair of adjacent coextruded layers can be formed of a polyester, and the other layer in the pair can be formed of a polyamide.

Examples of polyesters include polyethylene terephthalate (PET) polymers and polybutylene terephthalate (PBT) polymers.

Examples of commercially available PET polymers include the Selar PT family of PET polymers (e.g., Selar PT 8307, Selar PT4274, Selar PTX280), which are commercially available from E. I. DuPont de Nemours (Wilmington, Del.), the Cleartuf family of PET polymers (e.g., Cleartuf 8006), which are commercially available from M&G Polymers (Apple Grove, W. Va.), the Traytuf family of PET polymers (e.g., Traytuf 1006), which are commercially available from the Shell Chemical Company (Houston, Tex.), and the Melinar family of PET polymers (e.g., Melinar 5922C), which are commercially available from E. I. DuPont de Nemours (Wilmington, Del.).

Examples of commercially available PBT polymers include the Celanex family of polymers, commercially available from Ticona (Summit, N.J.), the Riteflex family of polymers, commercially available from Ticona (Summit, N.J.), the Hytrel family of PBT copolymers (e.g., Hytrel 5556, Hytrel 7246, Hytrel 4056), commercially available from E. I. DuPont de Nemours (Wilmington, Del.), and the Arnitel family of PBT copolymers (e.g., Arnitel EM630), commercially available from DSM (Erionspilla, Ind.).

Examples of polyamides include the nylon family of polymers, such as, for example, aliphatic nylons and aromatic nylons.

Examples of aliphatic nylons include nylon 12, nylon 6, nylon 6/10, nylon 6/12 and nylon 11. Nylon 12 is commercially available from, for example, Atofina (Philadelphia, Pa.). Nylon 12 is also commercially available as the Grilamid family of polymers from EMS (Sumter, S.C.) and as the Vestamid family of polymers from Daicel-Degussa Ltd. Nylon 6 is commercially available from, for example, Honeywell (Morristown, N.J.). Nylon 6/10 is commercially available from, for example, BASF (Mount Olive, N.J.). Nylon 6/12 is commercially available from, for example, Ashley Polymers (Cranford, N.J.). Nylon 11 is commercially available from EMS (Sumter, S.C.).

Examples of aromatic nylons include the Grivory family of polymers (commercially available from EMS (Sumter, S.C.)), nylon MXD-6 polymers (commercially available from Mitsubishi Gas Chemical (Tokyo, Japan)), and the Trogamid family of polymers (commercially available from Degussa AG (Germany).

Additional examples of polyamides include polyether block polyamide copolymers (commercially available, for example, as the Pebax family of polymers (e.g., Pebax 5533, Pebax 2533, Pebax 7033) from Atofina (Philadelphia, Pa.)).

In some embodiments, one or more of the layers in wall 10 is formed of a blend of polymers. As an example, in certain embodiments, one of the layers in a pair of adjacent coextruded layers may be formed of a blend of polymers, and the other layer in the pair may be formed of a single polymer. As another example, in some embodiments, one of the layers in a pair of adjacent coextruded layers may be formed of a blend of polymers, and the other layer in the pair may be formed of a blend of polymers.

In some embodiments, a blend contains more than one type of polyester. In certain embodiments, a blend contains more than one type of polyamide. In some embodiments, a blend contains at least one polyester and at least one polyamide.

In certain embodiments, a blend can include at least one adhesion enhancing material. An adhesion enhancing material can be used, for example, to enhance the adhesion between adjacent layers in wall 10. Examples of adhesion enhancing materials include epoxy or anhydride modified polyolefins, such as Lotader (Elf Atochem), Plexar (Equistar) and Kodar PETG (Eastman Kodak). Typically, an adhesion enhancing material is added to a material (e.g., a composition containing one or more polymers) prior to extrusion. For example, in embodiments in which adjacent layers are formed of PET and PBT, PETG can be added to the PET before extrusion.

In some embodiments, a blend can include a compatibilizing material (e.g., when the material from which a layer of wall 10 is formed contains a liquid crystal polymer (LCP)). The compatibilizing material can be a copolymer, such as a block copolymer, including moieties of at least two different chemical structures. The compatibilizing material can be a reactive polymer that reacts with the LCP and/or one or more other polymers in the blend. The compatibilizing material can be a catalyst that promotes a reaction between the LCP and one or more other polymers in the blend. Other compatibilizing materials can be used. Combinations of compatibilizing materials can be used. Examples of compatibilizing materials include copolyester elastomers, ethylene unsaturated ester copolymers, such as ethylene-maleic anhydride copolymers, copolymers of ethylene and a carboxylic acid or acid derivative, such as ethylene-methyl acrylate copolymers, polyolefins or ethylene-unsaturated ester copolymers grafted with functional monomers, such as ethylene-methyl acrylate copolymers, copolymers of ethylene and a carboxylic acid or acid derivative, such as ethylene-methyl acrylate maleic anhydride terpolymers, terpolymers of ethylene, unsaturated ester and a carboxylic acid or acid derivative, such as ethylene-methyl acrylate-methacrylic acid terpolymers, maleic acid grafted styrene-ethylene-butadiene-styrene block copolymers, and acrylic acid elastomers, such as acrylic rubbers. Similar polymers containing epoxy functional groups, for instance derived from glycidyl methylacrylate (e.g., alkyl (meth)acrylate-ethylene-glycidyl (meth)acrylate polymers) can be used. Ionomeric copolymers can be used. PETG can be used. Examples of compatibilizing materials include Hytrel HTR-6108, Polybond 3009 (BP Chemicals), SP 2205 (Chevron), DS1328/60 (Chevron), Lotader 2400, Escor ATX-320, Escor ATX-325, Vamac G1 and Lotader AX8660. In certain embodiments, a compatibilizing material (e.g., PETG) can be mixed with one or more polymers (e.g., an LCP-containing material) prior to extrusion.

Examples of LCPs include polyester(s), polyamide(s) and/or their copolymers, such as Vectra A (Ticona), Vectra B (Ticona) and Vectra LKX (Ticona) (e.g., Vectra LKX 1111 (Ticona)). Other LCPs and/or combinations of LCPs can be used.

One polymer blend product which can be used includes PET, a wholly aromatic LCP copolyester and an ethylene-methyl acrylate-acrylic acid terpolymer compatibilizing material, such as, for example, Escor ATX320, Escor ATX325, or Escor XV-11.04. Another polymer blend product includes PET, a wholly aromatic LCP copolyester and an ethylene-maleic anhydride copolymer compatibilizing material, such as Polybond 3009. Another polymer blend product includes PET, a wholly aromatic LCP copolyester and an ethylene-methyl acrylate copolymer grated with maleic anhydride compatibilizing material, such as DS 1328/60, or a copolyester elastomer, such as Hytrel HTR 6108. Polymer blend products including PET, LCP and at least two compatibilizing materials can be used. For example, DS1328/60 and Polybond 3009 can be used with the LCP Vectra. As an additional example, when the LCP is Vectra, the compatibilizing materials can be Polybond 3009 and at least one additional compatibilizing material selected from Escor ATX-320, Escor ATX-325, DS 1328160, Escor XV-11.04 and Hytrel HTR-6108.

In some embodiments in which a layer of wall 10 contains an LCP, a thermoplastic polymer and compatibilizing material(s), the blend product includes from about 0.1 weight percent to about 10 weight percent (e.g., from about 0.5 weight percent to about 2 percent) LCP, from about 40 weight percent to about 99 weight percent (e.g., from about 85 weight percent to about 99 weight percent) thermoplastic polymer, and from about 0.1 weight percent to about 30 weight percent (e.g., from about one weight percent to about 10 weight percent) compatibilizing material(s).

While certain polymers and polymer combinations are discussed above, other polymers and polymer combinations can also be used. Other polymers include, for example, elastomers such as thermoplastic elastomers and engineering thermoplastic elastomers. Additionally or alternatively, other polymers include copolymers such as ABS (acrylonitrile-butadiene-styrene), ABS/nylon, ABSApolyvinyl chloride (PVC), ABS/polycarbonate, acrylonitrile copolymer, polyacrylamide, polyacrylate and polyacrylsulfone, polyethylene naphthalate (PEN), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN), ethylene, propylene ethylene vinylacetate and ethylene vinyl alcohol (EVA), various ionomers, polyethylene type I-IV, polyolefins, polyurethanes, polyvinyl chloride, and polysiloxanes (silicones). Those with low to medium melt temperatures include fluorocarbons such as polychlorotriethylene (CTFE), poly[ethylene-co-chlorotrifluoroethylene] (ECTFE) copolymer ethylene tetrafluoroethylene (ETFE), copolymer tetrafluoroethylene and hexafluoropropylene (FEP), perfluoroalkane (PFA) and poly[vinylidene fluoride] (PVDF). One or more polycarbonates may also be used.

In certain embodiments, balloon 6 can have a burst pressure of at least about 12 atmospheres (e.g., at least about 16 atmospheres, at least about 20 atmospheres, at least about 22 atmospheres, at least about 24 atmospheres). The burst of a balloon is measured as follows. The balloon is deflated and submerged in a water bath at 37° C. The balloon is then inflated with nitrogen gas at a rate of about one atmosphere or less per second until the balloon bursts.

In some embodiments, balloon 6 can have a burst strength of at least about 10,000 psi (e.g., at least about 14,000 psi, at least about 18,000 psi, at least about 20,000 psi, at least about 25,000 psi, at least about 30,000 psi) and/or at most about 50,000 (e.g., at most about 45,000 psi, at most about 40,000 psi). The burst strength of a balloon is calculated as P(D)/2T, where P is the burst pressure of the balloon, D the nominal balloon diameter, and 2T the initial double-wall thickness of the balloon.

In certain embodiments, balloon 6 can have a puncture force of at least about 30 grams (e.g., at least about 40 grams, at least about 50 grams, at least about 60 grams). The puncture force of a balloon (e.g., a 3 millimeter balloon) is measured as follows. The balloon is submerged in a 37° C. water bath. The balloon is then inflated, and a 60° conical point pin is driven into the balloon at a rate of about 0.05 millimeter per second until the balloon is punctured.

In some examples, balloon 6 can pass the multiple inflation test. The multiple inflation test of a balloon is performed as follows. The balloon is deflated and submerged in a water bath at 37° C. The balloon is inflated to the rated burst pressure of the balloon over the course of about 10 seconds, held at the rated burst pressure for about 30 seconds, and then deflated to a vacuum. A balloon is considered to have passed the multiple inflation test if the inflate/hold/deflate procedure is repeated 40 times with substantially no delamination or defect formation as determined by inspection with a microscope (10× magnification).

In general, balloon 6 can be of any desired shape and size (e.g., coronary balloons, aortic balloons, peripheral balloons, reperfusion balloons, endoscopy balloons, urology balloons and neurology balloons). In certain embodiments, a coronary balloon can have a diameter of from about 1.5 millimeters to about six millimeters. In some embodiments, a peripheral balloon can have a diameter of from about three millimeters to about 12 millimeters. In certain embodiments, an endoscopy and/or urology balloon can have a diameter of from about four millimeters to about 40 millimeters. In some embodiments, a neurology balloon can have a diameter of from about 1.5 millimeters to about five millimeters.

Balloon 6 can have a double wall thickness (twice the nominal thickness through a single sidewall of the balloon) of at least about 0.0001 inch (e.g., at least about 0.0005 inch, from about 0.0005 inch to about 0.006 inch, from about 0.0008 inch to about 0.004 inch, about 0.001 inch to about 0.003 inch, about 0.0022 inch, about 0.0015 inch) for inflatable diameters of about 1.5 mm to about 6.0 mm. Smaller diameter balloons typically have thinner walls.

In general, the thickness of the layers of wall 10 can be varied as desired. In certain embodiments, the thickness of the layers in wall 10 varies progressively. For example, the layers may get thicker from the outermost layer to the innermost layer or vice versa. The thickness of the layers of one type of polymer may vary while the thickness of other layers may be constant.

In some embodiments, one or more of the layers can have a minimum thickness of at least about 0.02 micron (e.g., at least about 0.05 micron, at least about 0.1 micron, at least about 0.25 micron, at least about 0.5 micron, at least about 0.75 micron, at least about one micron, at least about 1.5 microns, at least about 2 microns, at least about 2.5 microns, at least about 3 microns, at least about 3.5 microns) and/or a maximum thickness of at most about 20 microns (e.g., at most about 15 microns, at most about 10 microns, at most about nine microns, at most about eight microns, at most about seven microns, at most about six microns, at most about five microns, at most about four microns, at most about three microns, at most about two microns, at most about one micron, at most about 0.5 micron, at most about 0.25 micron).

Typically, the medical devices (e.g., balloons, tubes, catheter shafts) are prepared by an extrusion process. Generally, this process can involve the use of an extrusion apparatus (e.g., a crosshead, such as a compact crosshead) having a series of discs. In certain embodiments, the thickness of one or more of the discs (e.g., at least two discs, at least three discs, at least four discs, at least five discs, at least six discs, at least seven discs, at least eight discs, at least nine discs, at least 10 discs, at least 11 discs, at least 12 discs, at least 13 discs, at least 20 discs, etc., each disc) can be less than about one inch (e.g., less than about 0.75 inch, less than about 0.5 inch, less than about 0.4 inch, less than about 0.3 inch, less than about 0.2 inch, less than about 0.15 inch, less than about 0.1 inch, less than about 0.05 inch) in the direction parallel to the flow of material (polymer) through the apparatus (e.g., in the direction L shown in FIG. 3). In certain embodiments, the thickness of at least one of the discs can be about one inch or less (e.g., about 0.75 inch or less, about 0.5 inch or less, about 0.4 inch or less, about 0.3 inch or less, about 0.2 inch or less, about 0.15 inch or less, about 0.1 inch or less) in the flow direction.

Figure 3:
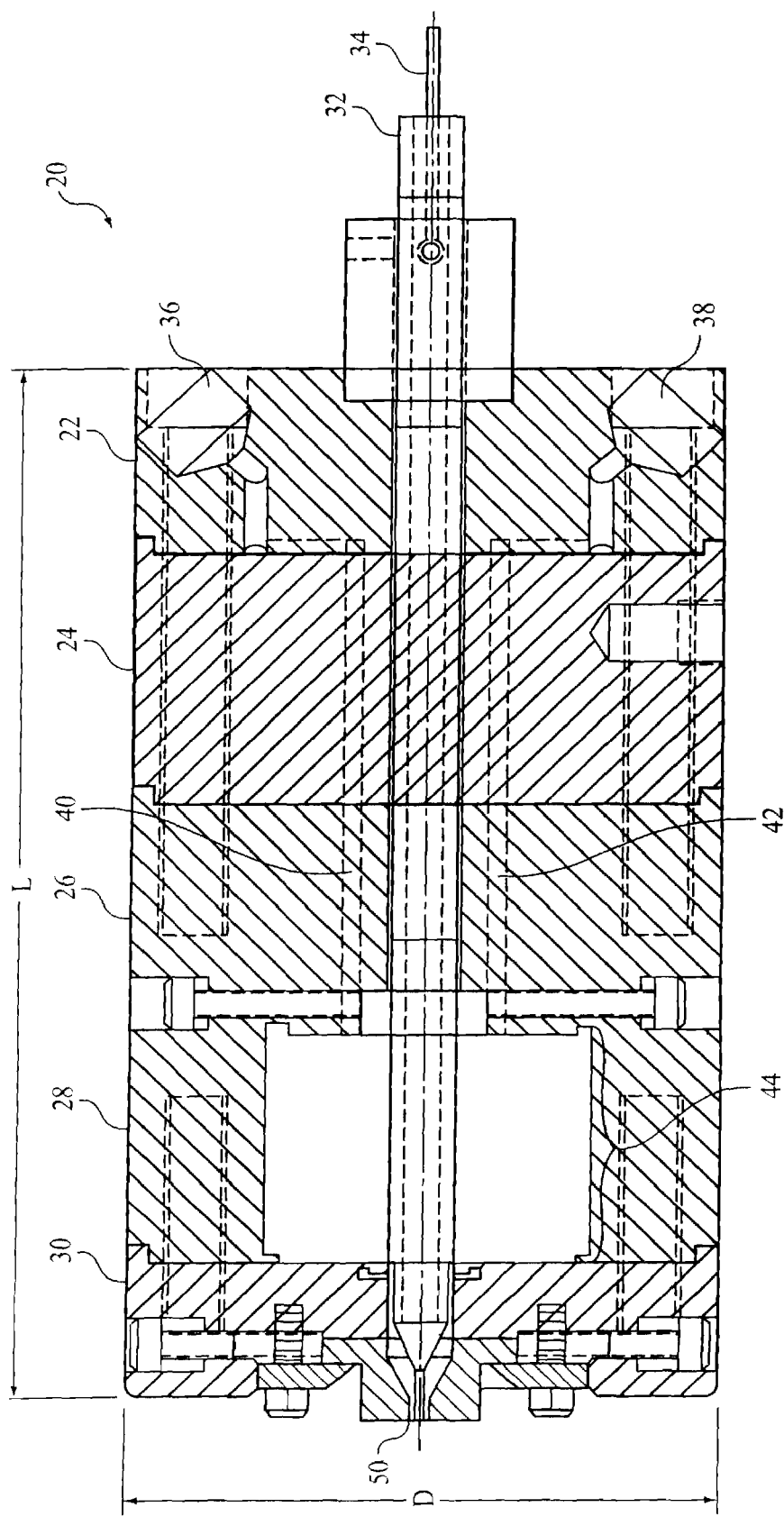
FIG. 3 is an assembly drawing of an embodiment of an extrusion crosshead.

FIG. 3 shows a cross-sectional view of an embodiment of an extrusion apparatus (a compact crosshead) 20 that can be used in the preparation of a multilayer balloon or tube. The tubes and balloons may be formed by first coextruding a multilayer tube having the desired sequence of layers (e.g., alternating layers containing a relatively high apparent shear viscosity polymer and layers containing a relatively low apparent shear viscosity polymer). Compact crosshead 20 that includes a series of assembly sections 22, 24, 26, 28, 30 with a common bore into which is placed a spacing mandrel 32 that encompasses an air supply tube 34. The assembly sections 22, 24, 26 define inlets 36, 38 from separate extruders (not shown) which feed different polymers (in this example polymer A and polymer B) into the head and include passageways 40, 42 which direct the polymers to assembly section 28 with a region 44 designed to house a series of extrusion discs.

Figure 4:
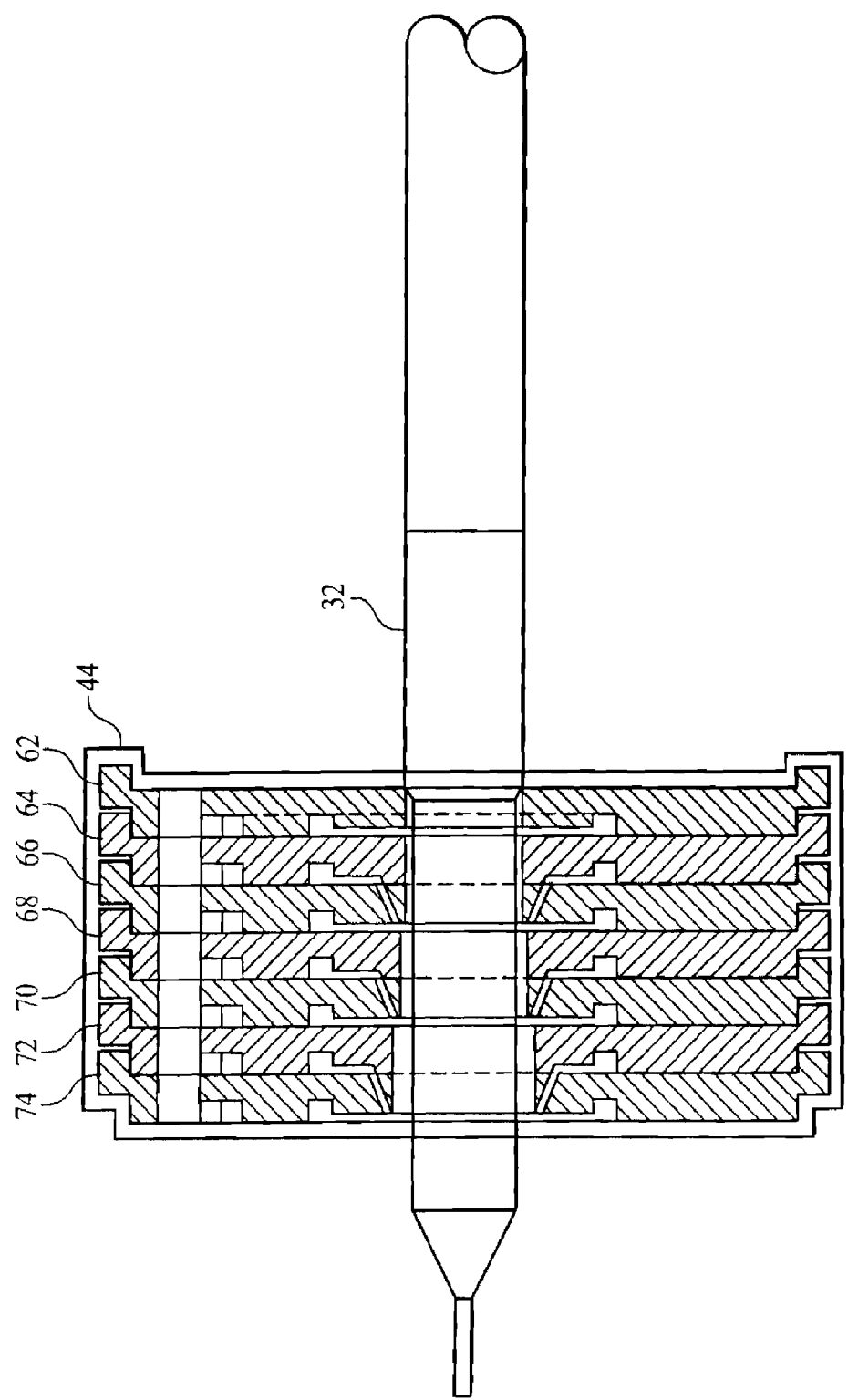
FIG. 4 is a cross-section view of a portion of an embodiment of an extrusion crosshead.

FIG. 4 shows a cross-sectional view of an assembly of seven extrusion discs 60, 62, 64, 66, 68, 70, 72 and 74 housed within region 44 (although depicted in FIG. 4 as having a gap between the discs and the walls that define region 44, in general the discs are disposed immediately adjacent the walls that define region 44). Discs 62, 66, and 70 have cone-shaped portions.

It has been observed that including a cone-shaped portion in one or more of the discs (e.g., in alternating discs) when one or more of the layers (e.g., alternate layers) contain at least one relatively high apparent shear viscosity polymer results in extruded medical devices (e.g., rubes) that have relatively high uniformity, little mixing of adjacent layers, and/or little (e.g., no) contact between alternate layers. The tubes can be processed to form, for example, balloons that demonstrate desirable properties (e.g., good hoop strength, good toughness, good crack resistance and/or good resistance to pinhole formation). Without wishing to be bound by theory, it is believed that including a cone-shaped portion in one or more of the discs (e.g., in alternating discs) can result in a more uniform flow and distribution of the polymers during extrusion, which can result in multilayer articles (e.g., multilayer tubes, multilayer balloons) with relatively well defined layers, relatively high uniformity, and/or relatively little intermixing of polymers between layers.

Discs 60, 62, 64, 66, 68 and 70 include passageways for both the relatively high apparent shear viscosity polymer and the relatively low apparent shear viscosity polymer, but an extrusion inlet and outlet for only one of the polymers. Disc 72 includes a passageway for only one polymer (e.g., the relatively high apparent shear viscosity polymer). In this way, the polymer flow continues along the assembly but each polymer is added to the extrusion stream in the desired order. For example, every other disc can have an inlet and outlet for the relatively high apparent shear viscosity polymer and every other intervening disc can have an inlet and outlet for the relatively low apparent shear viscosity polymer.

FIGS. 5A-5G show cross-sectional views of embodiments of the channel designs of discs 60, 62, 64, 66, 68, 70 and 72, respectively. The inlets and outlets of the discs are formed as machined channels in the face of the discs. Each disc includes a passageway 50 for the flow of one polymer referred to as "polymer A" (e.g., the relatively low apparent shear viscosity polymer), and a passageway 51 for the flow of the other polymer referred to as "polymer B") (e.g., the relatively high apparent shear viscosity polymer). Each disc also includes an opening 55 for an alignment pin is provided for registration of the discs. The outlets are formed by channels 56 that lead to gaps between adjacent discs. Each disc has a thickness t in the flow direction of the polymers.

Figure 5A:
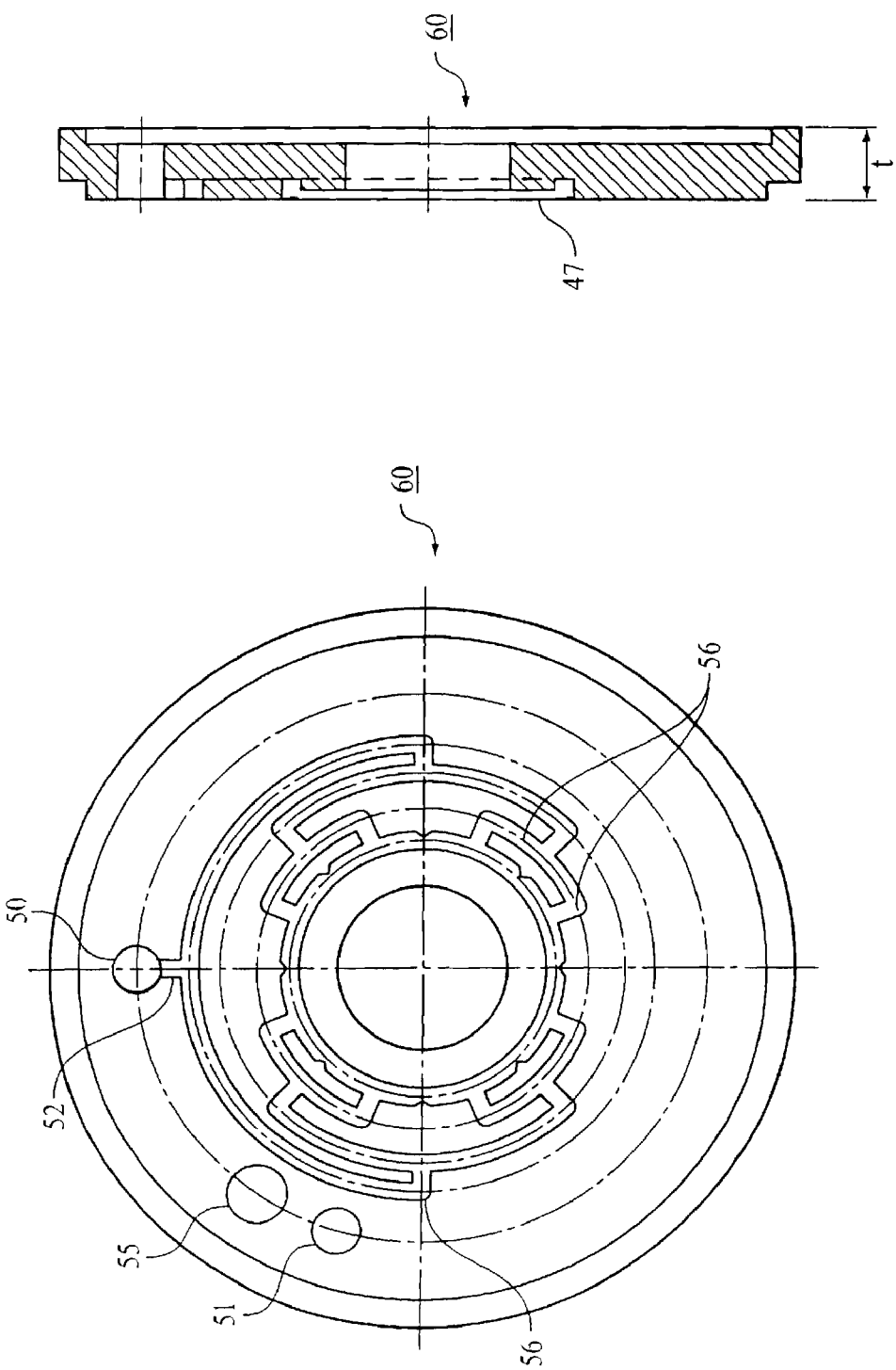
FIGS. 5A-5G are cross-sectional views of embodiments of crosshead discs.

As shown in FIG. 5A, disc 60 has an inlet 52 and an outlet 47 for polymer A, but no inlet or outlet for polymer B.

Figure 5B:
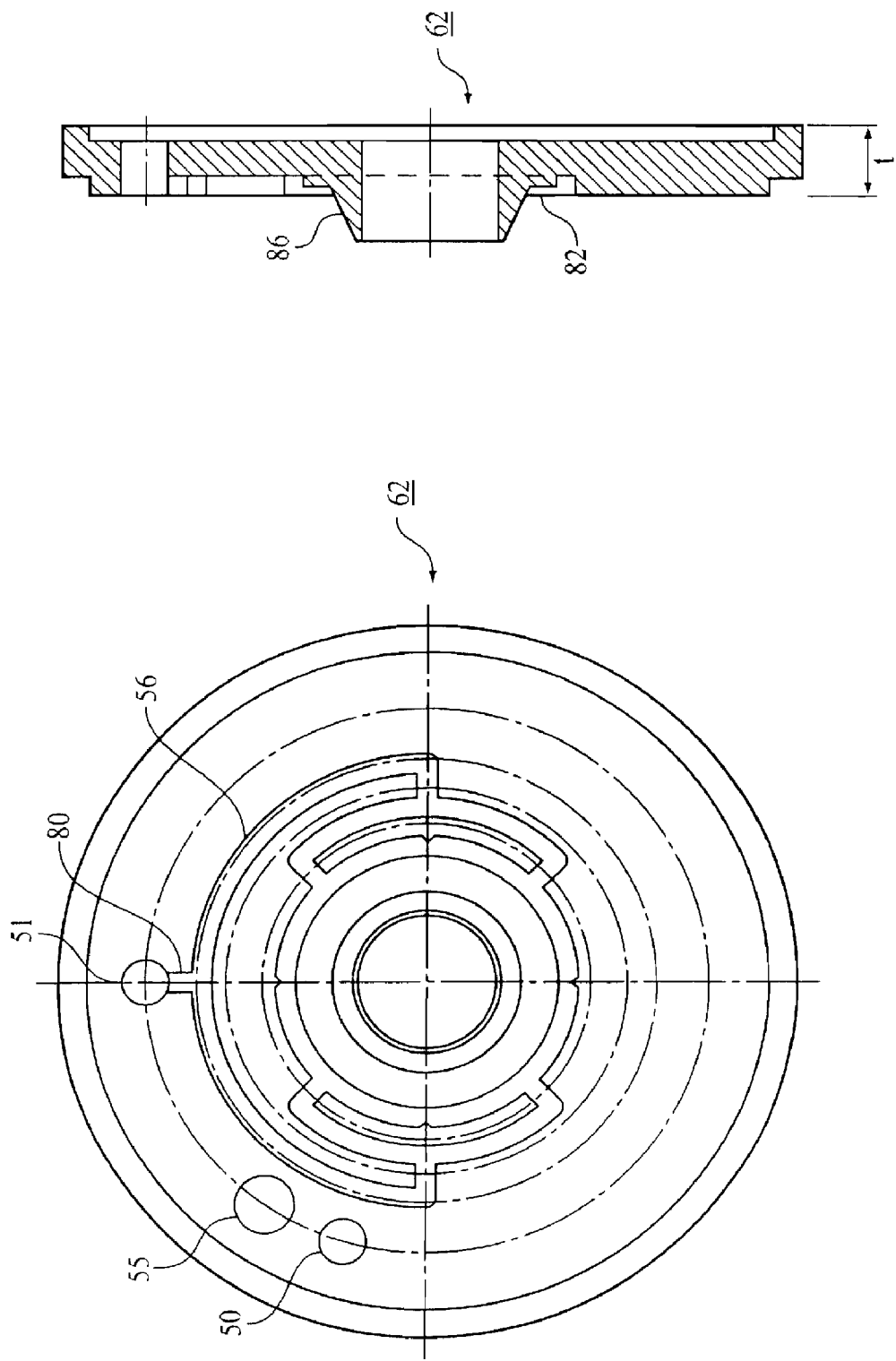

As shown in FIG. 5B, disc 62 has an inlet 80 and an outlet 82 for polymer B, but no inlet or outlet for polymer A. Disc 62 also includes a cone-shaped portion 86 that extends beyond thickness t of disc 62.

Figure 5C:
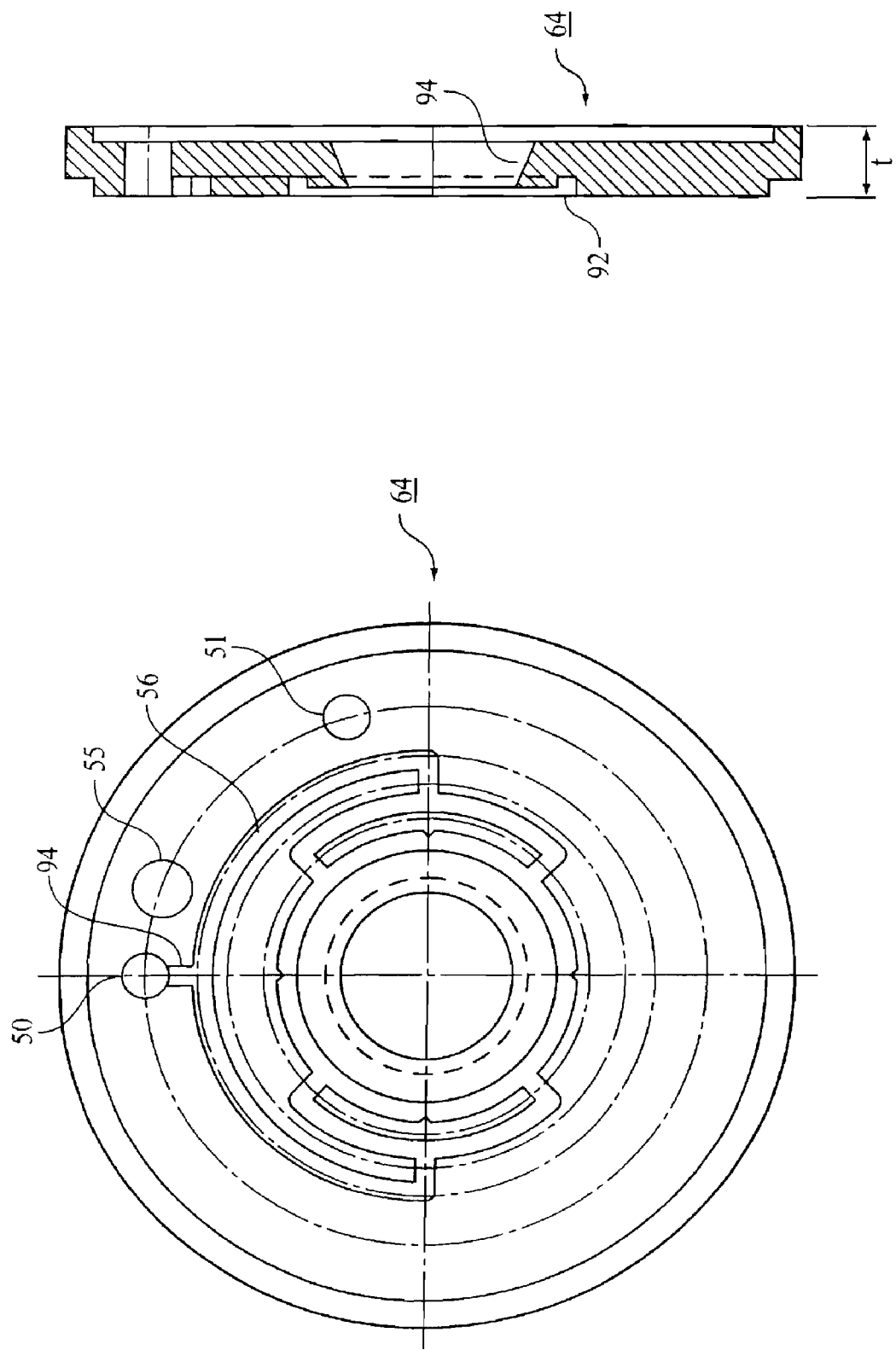

As shown in FIG. 5C, disc 64 has an inlet 90 and an outlet 92 for polymer A, but no inlet or outlet for polymer B. Disc 64 also has a cone-shaped portion 94 into which portion 86 of disc 62 fits.

Figure 5D:
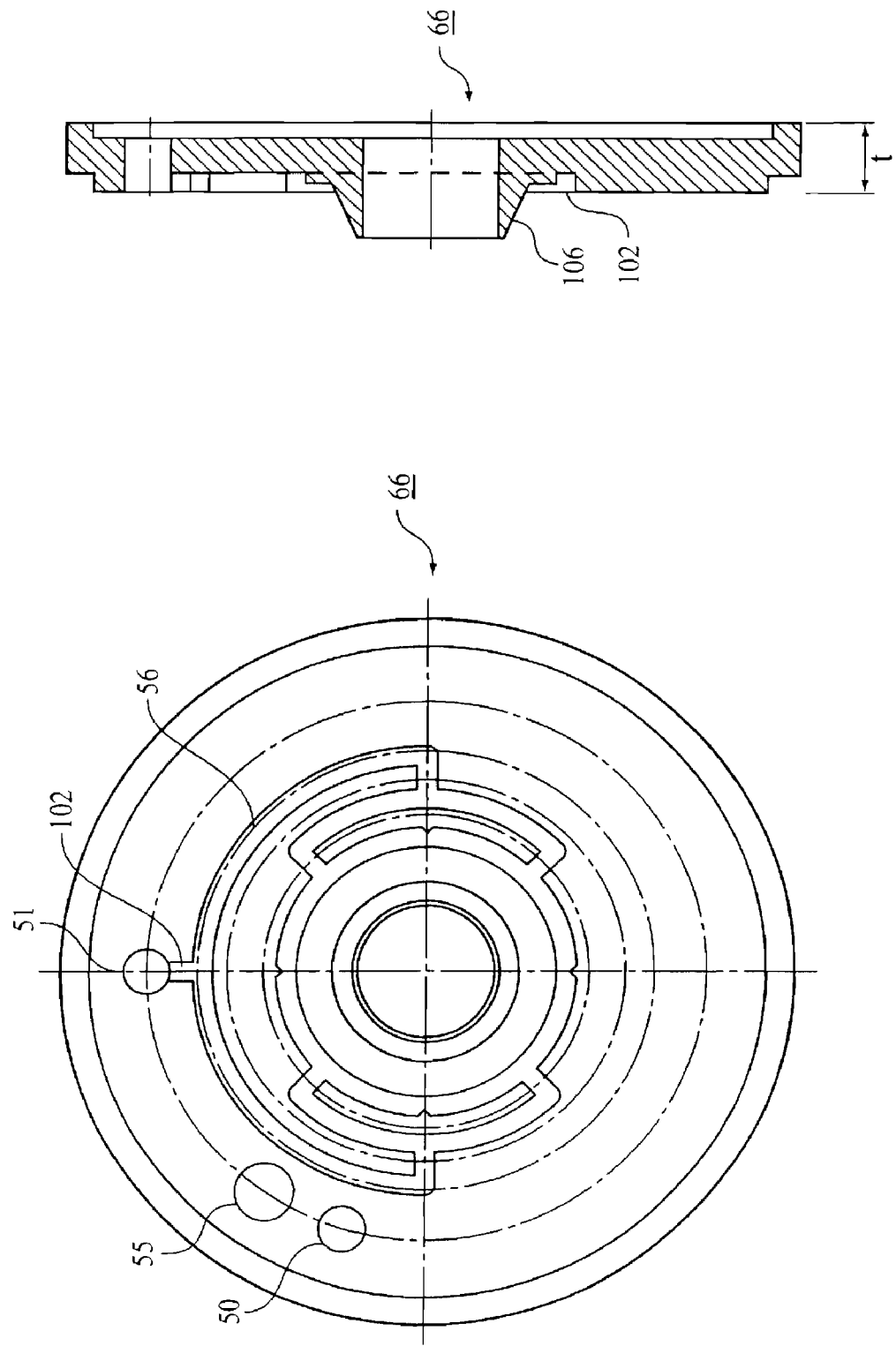

As shown in FIG. 5D, disc 66 has an inlet 100 and an outlet 102 for polymer B, but no inlet or outlet for polymer A. Disc 62 also includes a cone-shaped portion 106 that extends beyond thickness t of disc 66.

Figure 5E:
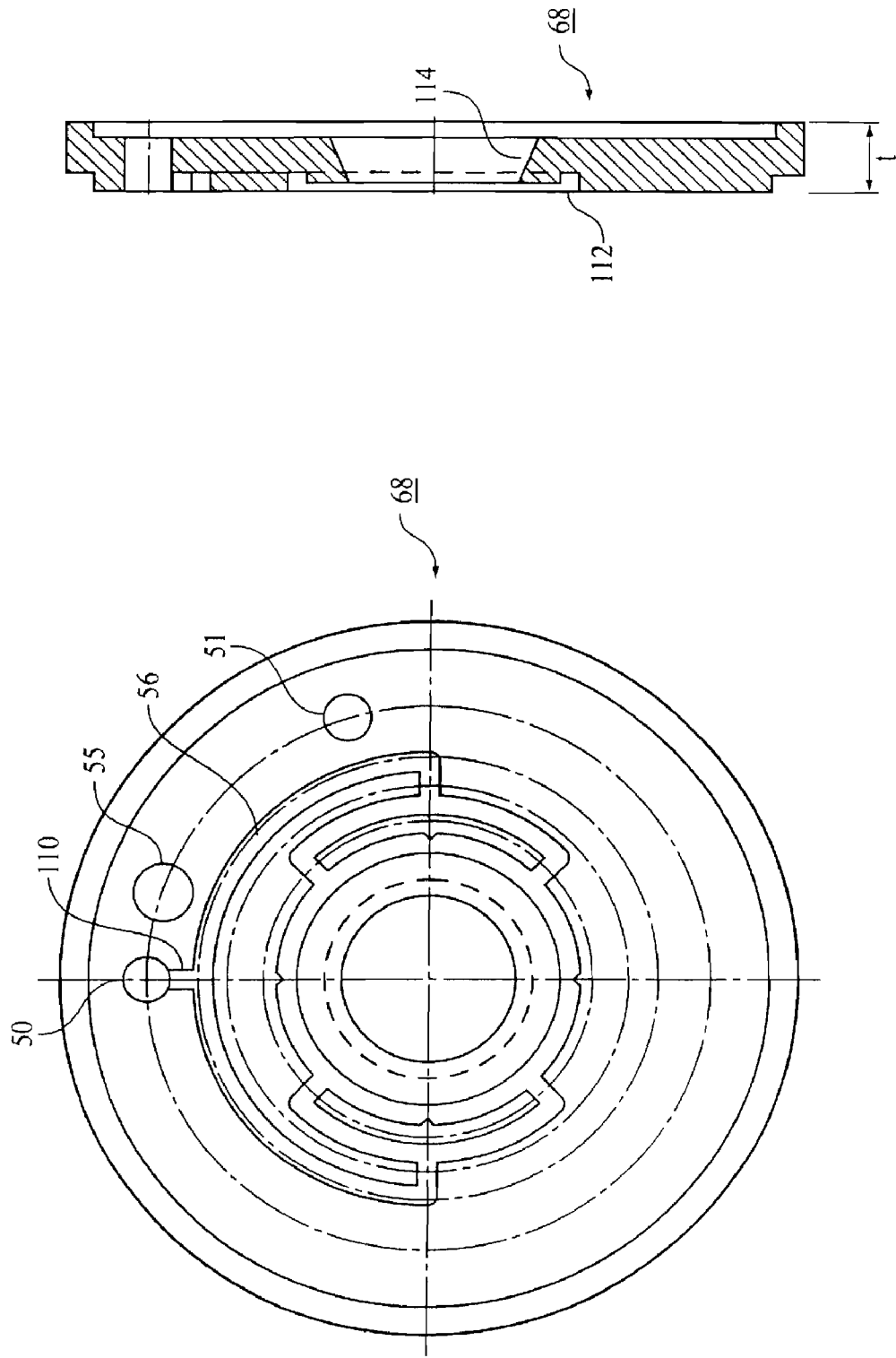

As shown in FIG. 5E, disc 68 has an inlet 110 and an outlet 112 for polymer A, but no inlet or outlet for polymer B. Disc 68 also has a cone-shaped portion 114 into which portion 106 of disc 66 fits.

Figure 5F:
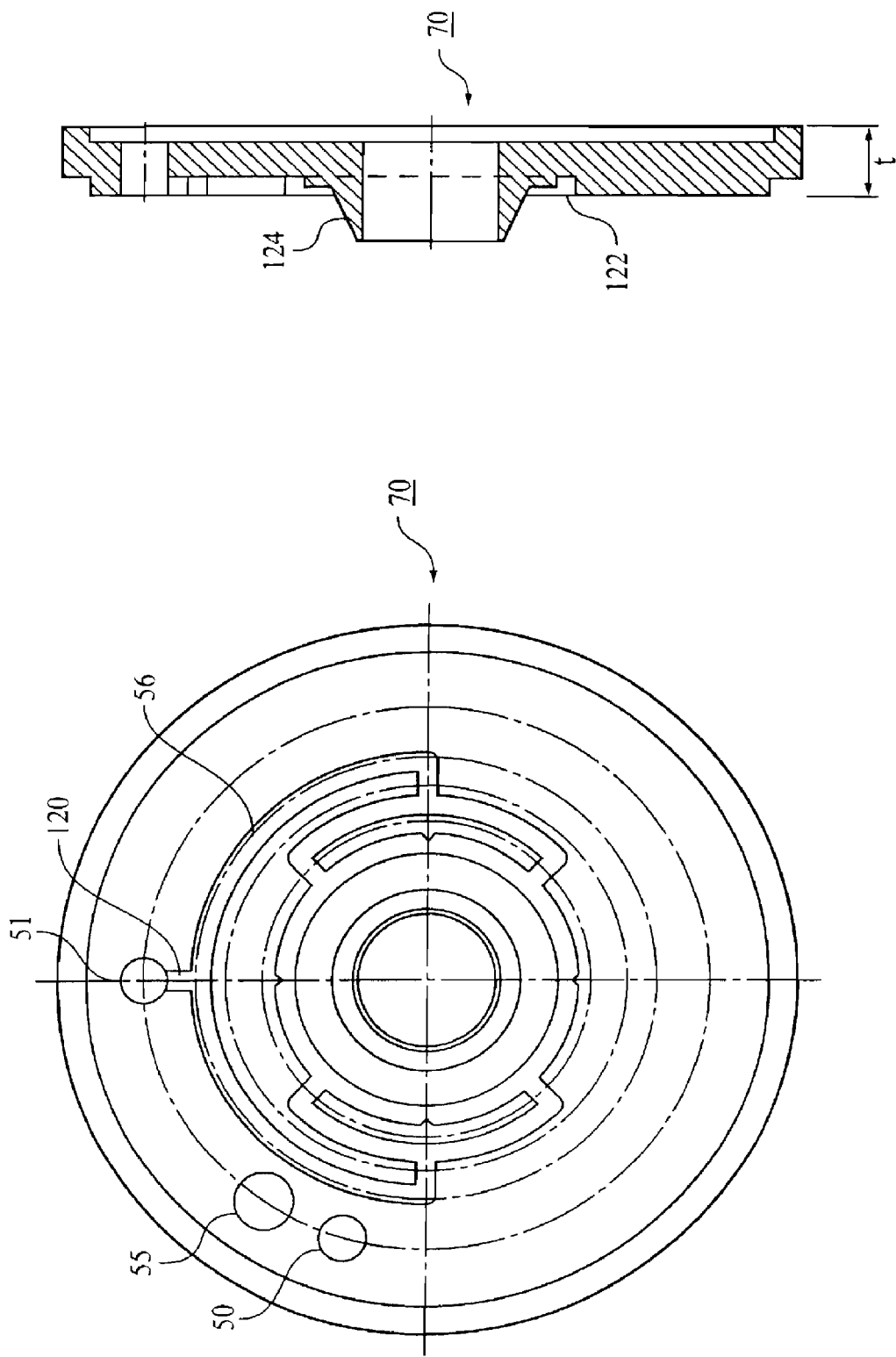

As shown in FIG. 5F, disc 70 has an inlet 120 and an outlet 122 for polymer B, but no inlet or outlet for polymer A. Disc 62 also includes a cone-shaped portion 126 that extends beyond thickness t of disc 70.

Figure 5G:
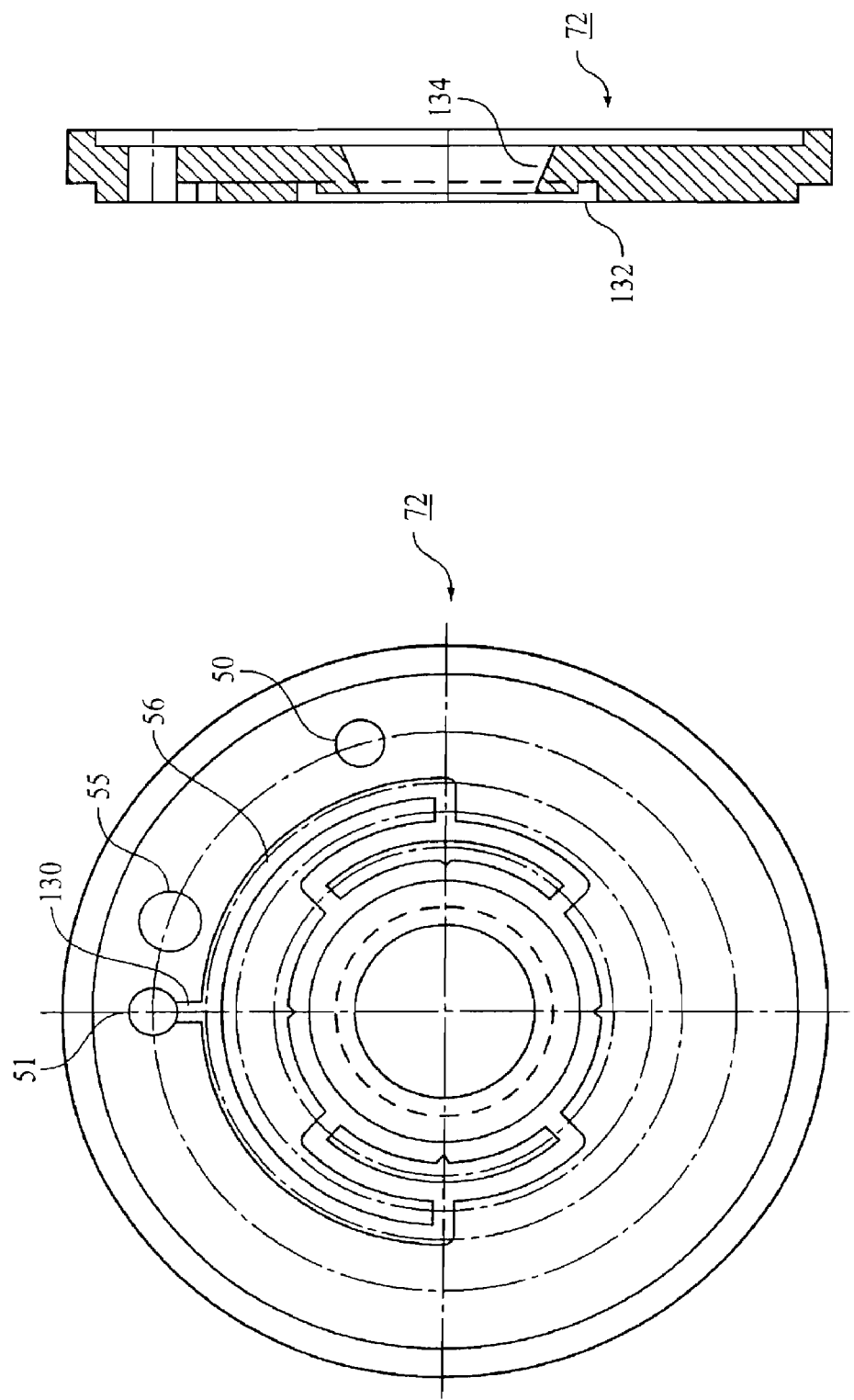

As shown in FIG. 5G, disc 72 has an inlet 130 and an outlet 132 for polymer A, but no inlet or outlet for polymer B. Disc 68 also has a cone-shaped portion 134 into which portion 126 of disc 70 fits.

With this arrangement of discs, the tube formed by the extrusion process will have its innermost layer formed of polymer A (e.g., the relatively low apparent shear viscosity polymer). The subsequent layers alternating between polymer B (e.g., the relatively high apparent shear viscosity polymer) and polymer A, with the outermost layer being formed of polymer A.

The crosshead provides for substantial flexibility in a compact design by changing the discs or outlet configurations of the discs to obtain a desired sequence of layers. For example, the diameter of the central opening in the discs can vary to facilitate polymer delivery along the stream. In addition, the channels can be arranged to direct polymer(s) into the stream at different radial orientations in successive discs. The number of layers can be varied from a single layer, two layers, three layers or more layers by controlling the number of discs.

The material from which the assembly sections and/or discs is formed can be varied as desired. In some embodiments, the assembly sections and the discs are formed of stainless steel.

In general, the length L and diameter D of the extrusion apparatus are not limited to any particular values. In certain embodiments, D is about 3.5 inches, and L is about 6.5 inches.

Various types of extruders can be used in the extrusion process. In some embodiments, the extruder is a Brabrender extruder (NJ).

The process parameters can be adjusted as appropriate for the particular materials used.

In general, the temperatures used should be high enough to allow the material to soften (e.g., melt) to a sufficient degree such that the material can flow at the pressure used without causing substantial thermal degradation of the material. As an example, the extrusion temperatures used for the Melinar 5922C layers can be, for example, from about 540° F. to about 600° F. In some embodiments, the temperatures used for Melinar 5922C can be 560° F., 570° F., 580° F., 590° F. and 590° F. As another example, the extrusion temperatures for an 80% Hytrel 7246/20% Hytrel 5556 blend can be from about 400° F. to about 475° F. In certain embodiments, the temperatures used for 80% Hytrel 7246/20% Hytrel 5556 blend can be 420° F., 450° F., 450° F., 450° F., 450° F. and 450° F.

Generally, the pressures used should be high enough to allow the material to flow but not so high as to cause substantial damage to the extrusion apparatus or substantial material leakage from the extrusion apparatus. Typically, the crosshead pressure is about 5,000 psi or less (e.g., about 4,000 or less, from about 3,000 psi to about 2,000 psi). For example, in some embodiments, the crosshead pressure is about 3820 psi.

In some embodiments, the screw speed for a relatively high apparent shear viscosity polymer can be from about 15 revolutions per minute (rpm) to about 30 rpm (e.g., about 22 rpm). In certain embodiments, the screw speed for a relatively low apparent shear viscosity polymer can be about 15 rpm to about 25 rpm (e.g., 20 rpm). In some embodiments, the crosshead temperature can be about from about 500° F. to about 550° F. (e.g., about 530° F.). In certain embodiments, the line speed can be from about 60 feet per minute (fpm) to about 80 fpm (e.g., about 71.8 fpm). In some embodiments, the die can be from about 0.10 inch to about 0.20 inch (e.g., about 0.150 inch). In certain embodiments, the tip can be from about 0.025 inch to about 0.075 inch (e.g., about 0.050 inch). In some embodiments, the water temperature can be about 40° F.

Figure 6:
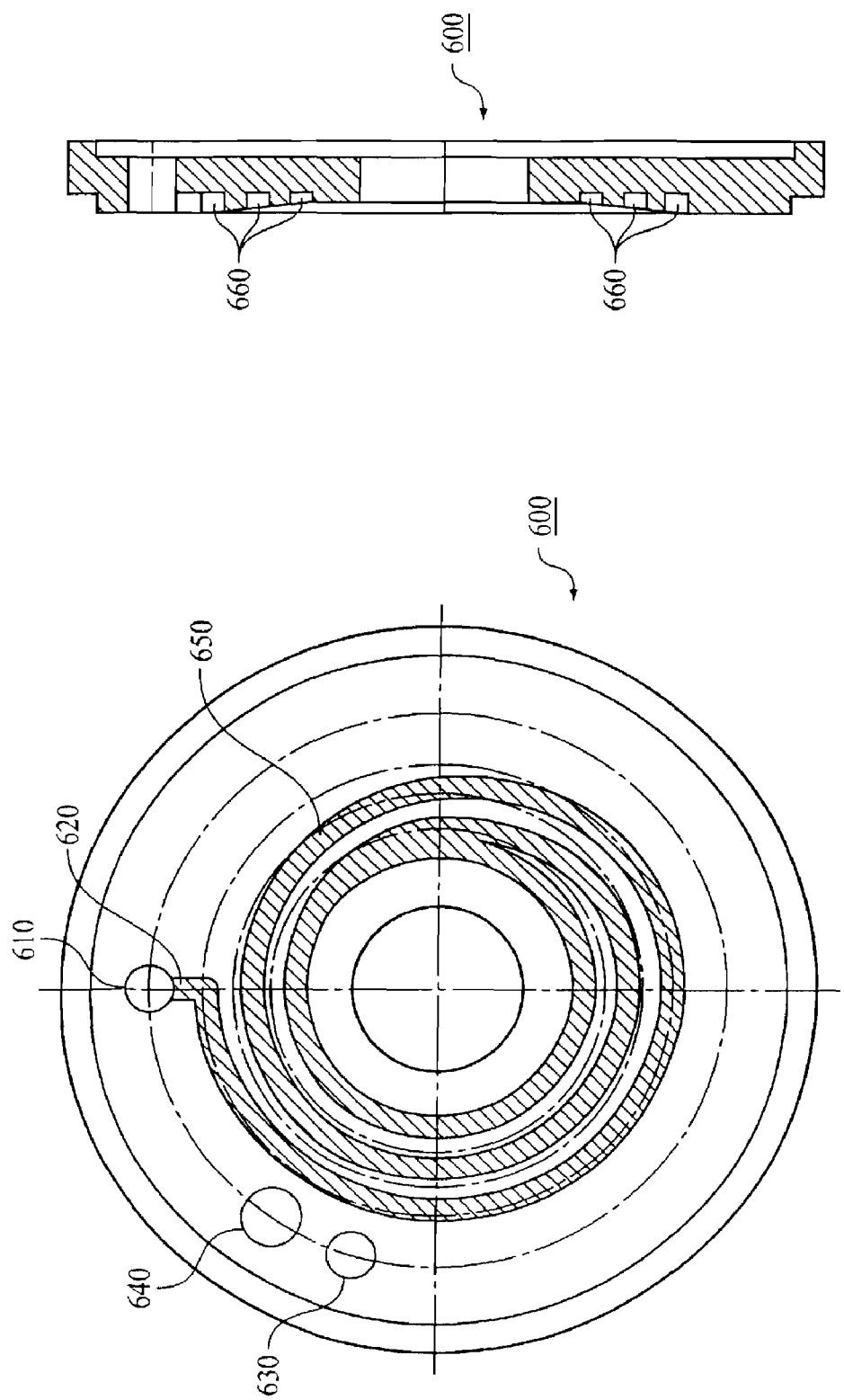
FIG. 6 is a cross-sectional view of a crosshead disc.

In some embodiments, the channels within the discs can have a spiral-shaped design. Typically, such discs do not also have the cone-shaped portions described above. FIG. 6 shows an embodiment of a disc 600 having a passageway 610 for polymer A (e.g., a relatively low apparent shear viscosity polymer), an inlet 620 for polymer A, a passageway 630 for polymer B (e.g., a relatively high apparent shear viscosity polymer), an alignment opening 640, and a spiral-shaped channel 650. Disc 600 also includes gaps 660 over which polymer A flows. Without wishing to be bound by theory, it is believed that using a spiral shaped channel allows for a more even flow and distribution of the polymers during extrusion, which can result in articles (e.g., balloons, tubes) having relatively well defined layers, a relatively high degree of uniformity and/or a relatively small amount of polymer intermixing between layers.

In general, the spiral should be wide enough to allow substantially uniform material flow during extrusion but narrow enough so that the pressures used do not cause substantial damage to the extrusion apparatus or substantial material leakage. In some embodiments, a spiral can have a width of from about 0.05 inch to about 0.75 inch (e.g., about 0.062 inch).

Generally, the spacing between turns of a spiral should be wide enough to allow substantially uniform material flow during extrusion but narrow enough so that the pressures used do not cause substantial damage to the extrusion apparatus or substantial material leakage. In certain embodiments, the spacing between turns of a spiral can from about 0.25 inch to about 0.75 inch (e.g., about 0.050 inch).

It has been observed that using a spiral shaped design in one or more of the discs (e.g., all the discs) when one or more of the layers (e.g., alternate layers) contain one or more relatively high apparent shear viscosity polymers results in extruded medical devices (e.g., tubes) that have relatively high uniformity, little mixing of adjacent layers, and/or little (e.g., no) contact between alternate layers. The tubes can be processed to form, for example, balloons that demonstrate desirable properties (e.g., good hoop strength, good toughness, good crack resistance and/or good resistance to pinhole formation). Without wishing to be bound by theory, it is believed that including a spiral shaped design in one or more of the discs (e.g., all the discs) can result in a more uniform flow (e.g., more uniform radial flow) and distribution of the polymers during extrusion due, at least in part, to the continuous and gradual distribution of flow in the radial direction. It is believed that the spiral shaped design can result in a relatively high pressure drop (e.g., more resistance) for a given space. It is believed that this can result in multilayer articles (e.g., multilayer tubes, multilayer balloons) with relatively well defined layers, relatively high uniformity, and/or relatively little intermixing of polymers between layers.

In embodiments, a balloon is formed from the extruded multi-layer tube by a stretch-molding process that includes necking the tube with a stretching machine at room temperature, followed by inserting the necked tube into a balloon mold of the desired diameter with the necking transition located at the cone area of the mold (the unstretched portion is formed into balloon body section). After the tubing section is securely inside the mold, the mold is placed in a fixture. The tubing section extends out the top of the mold and is fed into a Touhy clamp through which nitrogen gas is applied to the inner lumen of the tubing at forming pressure, with a tension of 60 grams applied to the tubing. The tubing section at the bottom of the mold is clamped off such that the pressure is maintained inside the tubing section. The mold is then gradually dipped into a deionized hot water bath maintained at about 95° C. (±1° C.) to a point just above the proximal waist portion of the mold at a controlled manner. A balloon is formed by radial expansion with internal pressure. After the balloon is formed, the mold is removed from the hot water bath and cooled for approximately 10 sec in a deionized water bath maintained at 10° C. Preferably, the process results in at least one (e.g., all) of the layers being biaxially oriented. Other processes can be used to form multilayer balloons (e.g., having at least one biaxially oriented layer) or tubes including dipping or spraying layers or fusing separately extruded concentrically arranged tubes.

The following examples are illustrative only and not intended as limiting.

Example 1

A sample of Cleartuf 8006 (M&G Polymers) was placed in a capillary rheometer (Kayeness Galaxy V, Model 8052) at about room temperature. The temperature of the capillary rheometer was set to 260° C., and the capillary rheometer was heated to that temperature, as reported by the capillary rheometer. The rheometer was held at that temperature for 10 minutes. The polymer was then extruded using a pressure such that the shear rate of the polymer, as reported by the capillary rheometer, was 660 per second. The shear viscosity reported by the capillary rheometer was 382 Pascal-seconds.

Example 2

Example 1 was repeated, but the temperature was 270° C. The shear viscosity reported by the capillary rheometer was 255 Pascal-seconds.

Example 3

Example 1 was repeated but the polymer was Melinar 5922C (E. I. DuPont de Nemours) and the temperature was 275° C. The shear viscosity reported by the capillary rheometer was 618 Pascal-seconds.

Example 4

Example 1 was repeated, but the polymer was Nylon MXD6007 (EMS) and the temperature was 245° C. The shear viscosity reported by the capillary rheometer was 650 Pascal-seconds.

Example 5

Example 4 was repeated, but the temperature was 260° C. The shear viscosity reported by the capillary rheometer was 555 Pascal-seconds.

Example 6

Example 1 was repeated, but the polymer was Nylon 6 (Zytel 275, E.I. DuPont de Nemours) and the temperature was 265° C. The shear viscosity reported by the capillary rheometer was 155 Pascal-seconds.

Example 7

Example 6 was repeated, but the temperature was 275° C. The shear viscosity reported by the capillary rheometer was 103 Pascal-seconds.

Example 8

Example 1 was repeated, but the polymer was a Hytrel 7246/Hytrel 5556 blend (E. I. DuPont de Nemours) and the temperature was 240° C. The shear viscosity reported by the capillary rheometer was 250 Pascal-seconds.

Example 9

Example 1 was repeated, but the polymer was Nylon 12 (Grilamid TR90, EMS) and the temperature was 270° C. The shear viscosity reported by the capillary rheometer was 250 Pascal-seconds.

Example 10

Example 1 was repeated, but the polymer was Pebax 7233 (Atofina) and the temperature was 210° C. The shear viscosity was reported by the capillary rheometer as 530 Pascal-seconds.

Example 11

Example 1 was repeated, but the polymer was Vectra LKX1107 (Ticona) and the temperature was 220° C. The shear viscosity reported by the capillary rheometer was 468 Pascal-seconds.

Example 12

Example 1 was repeated, but the polymer was Celanex (Ticona) and the temperature was 290° C. The shear viscosity reported by the capillary rheometer was 400 Pascal-seconds.

Example 13

Example 1 was repeated, but the polymer was a polycarbonate and the temperature was 300° C. The shear viscosity reported by the capillary rheometer was 350 Pascal-seconds.

Example 14

A seven layer tube of 0.0270 inch by 0.0650 inch was formed by coextruding Hytrel blend (80% Hytrel 7246 and 20% Hytrel 5556) (E. I. Dupont de Nemours, Wilmington, Del.) and Melinar 5922C PET (E. I. Dupont de Nemours, Wilmington, Del., intrinsic viscosity of about 1.1) in an alternate layer structure, with the odd numbered layers formed of the Hytrel blend and the even numbered layers formed of Melinar PET.

The extrusion temperatures used for the Melinar 5922C layers were 560° F., 570° F., 580° F., 590° F. and 590° F. The screw speed (one inch) for the Melinar 5922C was 22 revolutions per minute. The extrusion temperatures for the Hytrel Blend layers were 420° F., 450° F., 450° F., 450° F., 450° F. and 450° F. The screw speed (0.75 inch) for the Hytrel blend was 20 revolutions per minute. The crosshead temperature was 530°.F; and the line speed was 71.8 feet per minute. The die was 0.150 inch, and the tip was 0.050 inch. The crosshead pressure was 3820 psi; and the water temperature was 40° F. The apparatus was a spiral disk apparatus with each spiral having a width of 0.062 inch and a spacing between turns of about 0.050 inch.

A 4.5 millimeter balloon was formed from the tube at 95° C. and 420 pounds per square inch (psi) forming pressure. The tube was stretched at 90° C. (water bath) at a stretch ratio of 2.5. After stretching, the tube was quenched to room temperature. Then the stretched tube was necked at room temperature at the pressure of 630 psi to have smaller outer diameter distal waist section. The balloon had an average burst pressure of about 21.2 atmospheres, and a double wall thickness of about 0.00261 inch.

Example 15

Example 14 was repeated, except that an eight divider extrusion apparatus (without cone shaped portions or a spiral design) was used. The layers of the tube were not concentric, and alternate layers of material were in contact. The tube could not be processed to form a balloon following the procedure of Example 1.

Example 16

A tube was prepared as described in Example 14.

A 5.2 millimeter balloon was formed from the tube at 95° C. and 420 pounds per square inch forming pressure. The tube was stretched as described in Example 1. The balloon had an average burst pressure of about 21.5 atmospheres, and a double wall thickness of about 0.00240 inch.

Example 17

Example 16 was repeated, except that an eight divider extrusion apparatus (without cone shaped portions or a spiral design) was used. The layers of the tube were not concentric, and alternate layers of material were in contact. The tube could not be processed to form a balloon following the procedure of Example 3.

While certain embodiments have been described, the invention is not limited to these embodiments.

As an example, wall 10 can include a greater or lesser number of layers. In general, the number of polymer layers in wall 10 is greater than one (e.g., at least two, at least three, at least four, at least five, at least six, at least seven, at least eight, at least nine, at least 10, at least 11, at least 12, at least 13, at least 14, at least 15, at least 16, at least 17, at least 18, at least 19, at least 20, at least 30, at least 40, at least 50). In certain embodiments, the number of polymer layers in wall 10 is less than 100 (e.g., less than 90, less than 80, less than 70, less than 60, less than 50, less than 40, less than 35, less than 30, less than 25, less than 20, less than 15, less than 10).

Moreover, the number of pairs of adjacent coextruded layers formed of respective polymers having significantly different apparent shear viscosities can vary as desired. In certain embodiments, every pair of adjacent coextruded layers in wall 10 can be formed respective polymers having significantly different apparent shear viscosities. In some embodiments, fewer than all (e.g., all but one, all but two, all but three, all but four, all but five, all but six, all but seven, at but eight, all but nine, all but 10, etc.) of the pairs of adjacent coextruded layers are formed of respective polymers having significantly different apparent shear viscosities. In addition, the layers of wall 10 that are formed of high intrinsic viscosity material can, for example, be adjacent each other, alternate, or both (e.g., in one portion of the wall adjacent layers are formed of high intrinsic viscosity polymer, and in another portion of the wall layers formed of high intrinsic viscosity polymer alternate).

In addition, the manner in which wall 10 is prepared can be varied. As an example, an extrusion apparatus (e.g., a crosshead) having different dimensions can be used. As another example, various channel designs can be used in one or more of the discs, such as a spiral shaped channel that connects the inlet and outlet of a given disc. As an additional example, an extrusion apparatus can have more than one inlet for the polymer composition(s) (e.g., two inlets, three inlets, four inlets, five inlets, six inlets, seven inlets, eight inlets, nine inlets, 10 inlets, 11 inlets, 12 inlets, 13, inlets, 20 inlets, etc.). For example, an apparatus can have five inlets. In certain embodiments, an extrusion apparatus can include one inlet per disc.

Other embodiments are in the claims.

The invention claimed is:

1. An extrusion apparatus for making a multilayer article, the extrusion apparatus having a first end and a second end and a flow direction going from the first end to the second end, the extrusion apparatus comprising:
   a central mandrel having an axis;
   a plurality of discs where each disc surrounds the central mandrel, the plurality of discs including:
      a first pair of discs including a first disc and a second disc, the first disc having a central cone-shaped portion extending toward the second end and the second disc having a cone-shaped portion into which the cone-shaped portion of the first disc fits such that a gap exists between the two cone-shaped portions to form a polymer flow channel having an outlet,
      a third disc proximate the second disc,
   wherein the plurality of discs and the central mandrel define a cylindrical flow channel, and
   wherein the second disc and the third disc together define a gap creating a polymer flow channel having a portion that is perpendicular to the axis of the mandrel and wherein the perpendicular portion abuts the cylindrical flow channel at an outlet of the perpendicular portion; and
   a thickness of at least one of the discs in the flow direction is about one inch or less,
   wherein the outlets defined by the polymer extrusion channels of the first and second and second and third discs abut.

2. The apparatus of claim 1, wherein the polymer flow channel between the second disc and the third disc has a spiral-shaped component.

3. The apparatus of claim 2, further comprising a fourth disc, wherein the third disc has a central cone-shaped portion extending toward the second end and the fourth disc has a cone-shaped portion into which the cone-shaped portion of the third disc fits such that a gap exists between the two cone-shaped portions to form a polymer flow channel.

4. The apparatus of claim 3, further comprising a fifth disc and a sixth disc, wherein the fifth disc has a central cone-shaped portion extending toward the second end and the sixth disc has a cone-shaped portion into which the cone-shaped portion of the fifth disc fits such that a gap exists between the two cone-shaped portions to form a polymer flow channel
   wherein the fourth disc and the fifth disc together define a gap creating a polymer flow channel having a portion that is perpendicular to the axis of the mandrel and that abuts the cylindrical flow channel.

5. The apparatus of claim 4, wherein the polymer flow channel between the fourth disc and the fifth disc has a spiral-shaped component.

6. The apparatus of claim 1, wherein the thickness of the at least one disc in the flow direction is about 0.2 inch or less.

7. The apparatus of claim 1, wherein the apparatus is a crosshead extruder.

8. The apparatus of claim 2, wherein the spiral flow channel has a width of from about 0.05 inch to about 0.75 inch.

9. The apparatus of claim 1, wherein the at least one of the discs does not have a cone-shaped portion, wherein the at least one of the discs is one of the plurality of discs that defines a polymer flow channel with another disc.

10. An extrusion apparatus for making a multilayer article, the extrusion apparatus having a first end and a second end and a flow direction going from the first end to the second end, the extrusion apparatus comprising:
   a central mandrel having an axis;
   a plurality of discs where each disc surrounds the central mandrel, the plurality of discs including a first set of polymer flow channels and a second set of polymer flow channels, wherein the second set of polymer flow channels are interleaved in the first set of polymer flow channels such that no two channels of the first set are adjacent to each other and no two channels of the second set are adjacent to each other and wherein the polymer flow channels of the first and second sets each surround the central mandrel,
   wherein the central mandrel and the plurality of discs together form a cylindrical flow channel,
   where each of the polymer flow channels of the second set has an outlet and has a portion that extends away from the central mandrel perpendicular to the axis and that abuts the cylindrical flow channel and wherein each of the polymer flow channels of the second set includes a spiral-shaped component,
   wherein the outlets of at least one adjacent pair of one of the first set of the flow channels and one of the second set of the flow channels abut; and
   a thickness of at least one of the discs in the flow direction is about one inch or less.

11. The apparatus of claim 10, wherein each of the polymer flow channels of the first set are defined by an outlet and by a cone-shaped portion of a disc that extends toward the second end and a corresponding portion of an adjacent disc.

12. An extrusion apparatus for making a multilayer article, the extrusion apparatus having a first end and a second end and a flow direction going from the first end to the second end, the extrusion apparatus comprising:
   a plurality of discs where each disc has a central opening, the plurality of discs including:

a first pair of discs including a first disc and a second disc, the first disc having a central cone-shaped portion extending toward the second end and the second disc having a cone-shaped portion into which the cone-shaped portion of the first disc fits such that a gap exists between the two cone-shaped portions to form a polymer flow channel having an outlet, a second pair of discs including a third disc and a fourth disc, the third disc having a central cone-shaped portion extending toward the second end and the fourth disc having a cone-shaped portion into which the cone-shaped portion of the third disc fits such that a gap exists between the two cone-shaped portions to form a polymer flow channel, wherein the plurality of discs define an outer surface of a cylindrical flow channel, wherein the second disc and the third disc together define a gap creating a polymer flow channel having an outlet and extending perpendicular to the axis of the mandrel, wherein the polymer flow channel defined by the second and third disc abuts the cylindrical flow channel at a right angle to the axis, and wherein the outlets defined by the polymer extrusion channels of the first and second and second and third discs abut.

13. The apparatus of claim 12, wherein all but one of the discs includes a cone shaped portion extending substantially parallel to the flow direction.

14. The apparatus of claim 12, wherein the thickness of the at least one disc in the flow direction is about 0.75 inch or less.

15. The apparatus of claim 12, wherein the thickness of the at least one disc in the flow direction is about 0.15 inch or less.

16. The apparatus of claim 12, wherein each of the discs has a thickness in the flow direction that is about one inch or less.

17. The apparatus of claim 12, wherein the apparatus is a disc head extrusion apparatus.

18. The apparatus of claim 12, wherein the polymer flow channel between the second disc and the third disc has a spiral-shaped component.

19. The apparatus of claim 12, wherein each of the flow channels has a spiral-shaped component.

* * * * *